United States Patent [19]

Suga et al.

[11] Patent Number: 5,695,972
[45] Date of Patent: Dec. 9, 1997

US005695972A

[54] METHOD FOR PRODUCING L-ISOLEUCINE WITH A FERMENTATION PROCESS

[75] Inventors: Yasuichiro Suga, Yamaguchi, Japan; Masato Ikeda, Kensington, Calif.; Kuniki Kino, Yamaguchi, Japan

[73] Assignee: Kyowa Hakko Kogyo Co., Ltd., Tokyo, Japan

[21] Appl. No.: 653,042

[22] Filed: May 24, 1996

[30] Foreign Application Priority Data

May 31, 1995 [JP] Japan ................... 7-133404

[51] Int. Cl.$^6$ .................. C12P 13/06; C12P 13/08; C12N 1/20; C12N 1/00
[52] U.S. Cl. .................. 435/116; 435/115; 435/106; 435/252.8; 435/849
[58] Field of Search .................. 435/116, 115, 435/106, 252.8, 849

[56] References Cited

U.S. PATENT DOCUMENTS 4,411,991  10/1983  Hirakawa et al. .................. 435/42
5,474,918  12/1995  Kino et al. .................. 435/115

FOREIGN PATENT DOCUMENTS 5-130882  4/1993  Japan .
6-133787  5/1994  Japan .

OTHER PUBLICATIONS

Brock. Biology of Microorganisms, 3rd Ed, p. 355, 1979.
Herrmann and Somerville. Amino Acids–Biosynthesis and Genetic Regulation. 1983, pp. 148 and 246.

*Primary Examiner*—John W. Rollins
*Assistant Examiner*—Christopher R. Tate
*Attorney, Agent, or Firm*—Fitzpatrick, Cella, Harper & Scinto

[57] ABSTRACT

The present invention provide a method for the industrial production of L-isoleucine which is useful as pharmaceuticals, foods, feed additives and the like. The method comprises cultivating in a nutrient medium a microorganism belonging to the genus Escherichia which is capable of rapidly growing in a medium containing L-homoserine as the single nitrogen source and has an ability to produce L-isoleucine in the medium, producing and accumulate L-isoleucine in a culture and recovering L-isoleucine therefrom.

4 Claims, No Drawings

METHOD FOR PRODUCING L-ISOLEUCINE WITH A FERMENTATION PROCESS

FIELD OF THE INVENTION

The present invention relates to a method for producing L-isoleucine using a fermentation process. L-isoleucine is an amino acid which plays a nutritionally important role for both humans and animals and is used as pharmaceuticals, foods, feed additives and the like.

BACKGROUND OF THE INVENTION

Since isoleucine has four optical isomers, it is very difficult to economically produce L-isoleucine alone by chemical synthesis or by a combination of chemical synthesis and enzymatic partition. Thus, industrial production of L-isoleucine is performed mainly by a fermentation process.

As methods for producing L-isoleucine with a fermentation process, precursor addition methods are known wherein precursors for L-isoleucine such as DL-α-aminobutyric acid, α-ketobutyric acid and threonine are added to a fermentation medium or a microbial reaction system and converted into L-isoleucine (Japanese Examined Patent Publication Nos. 45347/60, 8709/68, 29789/71, etc.). However, the above-mentioned methods are not advantageous for industrial production, because they need expensive starting materials and result in low yields.

On the other hand, as direct fermentation methods wherein L-isoleucine is produced from sugar directly and accumulated in a culture broth, there are known methods which employ mutants induced from wild type strains of microorganisms belonging to the genera Corynebacterium, Brevibacterium, Escherichia, Serratia, Arthrobacter and the like. L-isoleucine producing mutants include, for example, auxotrophic strains which require amino acids or nucleic acids (Japanese Examined Patent Publication Nos. 7091/63 and 60237/89), strains having resistant mutation to amino acid analogs, vitamins and the like (Japanese Examined Patent Publication Nos. 21077/76, 62394/91, 62395/91; Japanese Unexamined Patent Publication Nos. 101582/75 and 130882/93), strains having both auxotrophic mutation and amino acid analogs-resistant mutation (Japanese Examined Patent Publication Nos. 6237/76 and 32070/79), strains having fluoropylvic acid-sensitive mutation (Japanese Examined Patent Publication No. 60236/89), strains with enhanced ability to grow utilizing L-aspartic acid as the sole nitrogen source (Japanese Examined Patent Publication No. 56596/92), or strains having a mutation of decreased substrate affinity in aminoacyl t-RNA synthase (Japanese Unexamined Patent Publication No. 330275/92). Furthermore, transformants produced by using recombinant DNAs including those genes involved in the biosynthesis of isoleucine or threonine are also known (Japanese Unexamined Patent Publication Nos. 893/83, 12995/85, 30693/85, 195695/86, 458/90, and 42988/90).

SUMMARY OF THE INVENTION

Recently, a demand for L-isoleucine for use in pharmaceuticals, foods, feeds, and so forth is increasing. Therefore, it is strongly desired to improve methods for producing L-isoleucine. Accordingly, it is an object of the present invention to provide an industrially efficient method for producing L-isoleucine which is useful as pharmaceuticals, foods or feed additives.

Microorganisms belonging to the genus Esherichia can not grow or grow very poorly in a medium containing L-homoserine as the sole nitrogen source. To date, there has not been known a method for producing L-isoleucine by using a microorganism belonging to the genus Escherichia which has acquired an ability to grow rapidly in the above-mentioned medium.

The present invention can provide a method for producing L-isoleucine comprising culturing in a nutrient medium a microorganism belonging to the genus Escherichia which is capable of growing rapidly in a medium containing L-homoserine as the sole nitrogen source and has an ability to produce L-isoleucine in the medium, producing and accumulating L-isoleucine in the culture, and recovering L-isoleucine therefrom.

Furthermore, the present invention provides a microorganism belonging to the genus Escherichia which is capable of growing rapidly in a medium containing L-homoserine as the sole nitrogen source and producing L-isoleucine in the medium.

DETAILED DESCRIPTION OF THE INVENTION

Hereinbelow, the present invention will be described in detail.

As the microorganism of the present invention, any microorganism may be used so long as it belongs to the genus Escherichia and can grow in a medium containing L-homoserine as the sole nitrogen source. Concretely, such a microorganism belonging to the genus Escherichia may be used which can form colonies more than 0.6 mm in diameter on the L-homoserine minimum agar plate medium described below when cultured at 30° to 35° C. for 3 to 7 days. The above-mentioned "L-homoserine minimum agar plate medium" is obtained by adding agar to a modified minimal medium (hereinafter referred to as "L-homoserine minimum medium") in which the nitrogen sources have been replaced with L-homoserine and which contains L-homoserine as the sole nitrogen source at a concentration of 0.01–0.1%. Examples of such microorganisms include *Escherichia coli* H-9146 and H-9156.

The L-Isoleucine producing strain of the present invention may be selected from those microorganisms which grow more rapidly than parent strains on the L-homoserine minimum agar plate medium. Microorganisms having such properties may be obtained by using known mutagenizing treatments, cell fusion, transduction, or other gene recombination techniques. In addition, those microorganisms may also have other properties to improve L-isoleucine productivity, such as auxotrophy, drug resistance, and drug sensitivity.

The production of L-isoleucine using the microorganism of the present invention may be carried out by conventional methods for bacterial culture.

As the medium used, any synthetic or natural medium may be used so long as it appropriately contains carbon sources, nitrogen sources, inorganic compounds, and traces amount of other nutrients required for the strain used.

As the carbon source, carbohydrates such as glucose, fructose, sucrose, lactose, molasses, cellulose hydrolysates, crude sugar hydrolysates, starch hydrolysates; organic acids such as pyruvic acid, acetic acid, fumaric acid, malic acid, and lactic acid; and alcohols such as glycerol, propanol and ethanol may be used.

As the nitrogen source, ammonia, ammonium salts of various inorganic acids and organic acids such as ammonium chloride, ammonium sulfate, ammonium acetate, and ammonium phosphate; other nitrogen-containing compounds; amines, peptone, meat extract, yeast extracts, trypton, corn steep liquor, casein hydrolysates, soybean cakes, soybean cake hydrolysates, various cultured cells of microorganisms, their digested products, etc. may be used.

As the inorganic compounds, potassium dihydrogen phosphate, dipotassium hydrogen phosphate, magnesium hydrogen phosphate, magnesium sulfate, magnesium chloride, sodium chloride, ferrous sulfate, manganese sulfate, copper sulfate, calcium chloride, calcium carbonate, etc. may be used.

The microorganism of the invention is cultivated under aerobic conditions by shaking culture, submerged-aerial stirring culture or the like at 20° to 40° C., preferably 28° to 37° C. The pH of the medium ranges from 5 to 9. Preferably, it is maintained almost neutral. The adjustment of pH is carried out with calcium carbonate, inorganic or organic acids, alkaline solutions, ammonia, pH buffering solution, etc. usually, L-isoleucine is produced and accumulated in the culture by 1 to 7 day culture.

After the completion of the cultivation, precipitates such as cells are removed from the culture by centrifugation, etc. By using a combination of ion exchange treatment, concentration, salting out or the like, L-isoleucine can be recovered from the supernatant.

According to the present invention, L-isoleucine is efficiently produced industrially.

PREFERRED EMBODIMENTS OF THE INVENTION

The present invention will be described below in more detail with reference to the following Examples 1–3.

EXAMPLE 1

Acquisition of L-isoleucine producing mutants capable of rapidly growing in the L-homoserine minimum medium L-isoleucine producing mutants capable of rapidly growing in the L-homoserine minimum medium were induced from 2 parent strains. Briefly, as the parent strains, the amino acid non-producing strain *Escherichia coli* ATCC 11105[J. Bacteriol., 60, 17(1950)] which has not received any mutagenizing treatment to improve its amino acid productivity and does not produce a detectable amount of amino acids in the culture and the L-isoleucine producing strain *Escherichia coli* H-8683(FERM BP-4052) were used.

According to known methods, both ATCC 11105 and H-8683 strains were treated with N-methyl-N'-nitro-N-nitrosoguanidine (0.5 mg/ml) as a mutagen at 33° C. for 30 minutes. Then, the treated strains were spread on the L-homoserine minimum agar plate medium (pH 7.2)(0.5% glucose, 0.02% L-homoserine, 0.3% potassium dihydrogen phosphate, 0.6% disodium hydrogen phosphate, 0.01% magnesium sulfate, 20 mg/liter calcium chloride, and 2% agar) supplemented with 20 mg/liter DL-methionine which is an auxotrophic amino acid. The cells were incubated at 33° C. for 4 to 7 days, and large colonies grown were separated as mutants which acquired an ability to grow rapidly in a medium containing L-homoserine as the sole nitrogen source.

Those mutants induced from ATCC 11105 were subjected to an L-isoleucine production test which was conducted according to the bioassay described below. In seven strains out of the one hundred mutants tested, a circular growth zone (halo)(which was formed by the growth of CGSC3516 strain and which shows the production of L-isoleucine) was observed. Among such halo forming mutants, the mutant which formed the largest halo was selected, and designated as *Escherichia coli* H-9146.

L-isoleucine production test by bioassay

The L-isoleucine auxotroph, *Escherichia coli* CGSC3516 (ilvE316, trp-3, his-4, thi-1)[J. Bacteriol., 98, 1179(1969)] is cultured in a natural medium (pH 7.2) (1% trypton, 0.5% yeast extract, 1% NaCl) for 24 hr. The cells are centrifuged and then washed with saline. These operations are repeated twice. After that, the cells are mixed with an agar medium for production test (0.5% glucose, 0.2% ammonium chloride, 0.3% potassium dihydrogen phosphate, 0.6% disodium hydrogen phosphate, 0.01% magnesium sulfate, 20 mg/liter calcium chloride, 20 mg/liter L-valine, L-leucin, L-tryptophan, L-histidine and DL-methionine, 1 mg/liter thiamin chloride salt, and 2% agar) (pH 7.2) to prepare a plate medium containing CGSC3516 strain at the final concentration of $10^6$ cells/ml. A strain to be tested for its L-isoleucine productivity is replicated on this plate medium, and then cultivated for 1 day at 33° C. After cultivation, the L-isoleucine productivity is evaluated based on the size of the circular growth zone formed around the test strain by CGSC3516 strain.

On the other hand, the mutant strains induced from the L-isoleucine producing strain H-8683 were subjected to an L-isoleucine production test which was conducted in a similar manner (using a thick test tube) to that described in Example 3. One hundred mutants were tested and, as a result, about 8% of the mutants showed an enhanced L-isoleucine productivity compared to the parent. Among such mutant strains, the mutant which produced the largest amount of L-isoleucine was selected and designated as *Escherichia coli* H-9156.

Both *Escherichia coli* H-9146 and H-9156 were deposited with National Institute of Bioscience and Human-Technology, Agency of Industrial Science and Technology, Japan, as of Mar. 28, 1996, under the accession numbers FERM BP-5055 and FERM BP-5056, respectively, both in terms of the Budapest Treaty.

EXAMPLE 2

Comparative growth test on the L-homoserine minimum agar plate medium

Two mutants, H-9146 and H-9156, obtained in Example 1 and the respective parent strains, ATCC 11105 and H-8633, were subjected to a competitive growth test on (20 mg/liter methionine containing) L-homoserine minimum agar plate medium described in Example 1, the medium containing L-homoserine as the sole nitrogen source. Each of these four strains was cultivated for 24 hr on the natural medium. After that, each strain was suspended in physiological saline. The cell suspension was spread on the agar plate medium at the concentration of 1 to 10 cells/cm², and incubated at 33° C. for 5 days. Then, the growth of each strain was compared based on the sizes of colonies formed. Results are shown in Table 1.

Both parent strains, ATCC 11105 and H-8683, grew very poorly on the above-mentioned L-homoserine minimum agar plate medium containing L-homoserine as the sole nitrogen source, and only formed colonies smaller than 0.5 mm in size. However, both H-9146 and H-9156 could form clear colonies larger than 1 mm in size on the same agar plate medium. These results demonstrate that the both mutant strains, H-9146 and H-9156, have acquired ability to grow rapidly utilizing L-homoserine as the sole nitrogen source.

TABLE 1

| Strain | Nitrogen source | |
|---|---|---|
| | None | L-homoserine (0.02%) |
| ATCC 11105 | − | ± |
| H-9146 | − | ++ |
| H-8683 | − | ± |
| H-9156 | − | + |

++; very good growth, colony size ≧ 3 mm
+; good growth, 1 mm ≦ colony size ≦ 3 mm
±; poor growth, colony size ≦ 0.5 mm
−; no growth, no colony formation

EXAMPLE 3

L-isoleucine Production Test

An L-isoleucine production test was performed on the two mutants, H-9146 and H-9156, both obtained in Example 1, and their parent strains, ATCC 11105 and H-8683, as follows.

Each of these 4 strains were inoculated into a thick test tube containing 6 ml of a seed culture medium (2% glucose, 1% peptone, 1% yeast extract, 0.25% NaCl, 130 mg/liter DL-methionine, and 1% calcium carbonate) (pH 7.0), and cultivated with shaking at 30° C. for 16 hr. One tenth milliliter of each seed culture broth was inoculated into 5 ml of a production medium (6% glucose, 0.2% corn steep liquor, 1.6% ammonium sulfate, 0.1% potassium dihydrogen phosphate, 100 mg/liter DL-methionine, 4% magnesium phosphate, and 1% calcium carbonate) (pH 7.0) and then cultivated at 30° C. for 48 hr with shaking. After that, the amount of L-isoleucine accumulated in the culture was determined by HPLC.

Results are shown in Table 2. The mutant H-9146 induced from the amino acid non-producing strain ATCC 11105 showed that it acquired an ability to produce a detectable amount of L-isoleucine outside the cells in the culture broth. Another mutant H-9156 induced from the L-isoleucine producing strain H-8683 showed an enhanced L-isoleucine producing ability. H-9156 could accumulate more L-isoleucine than the parent strain by about 13%.

Consequently, it has become clear that, by using the procedures described in Example 1, a mutant having an enhanced L-isoleucine producing ability can be induced not only from an L-isoleucine producing strain but also from an amino acid non-producing strain which has received no mutagenizing treatment to improve its amino acid productivity.

TABLE 2

| Strain | L-isoleucine (g/liter) |
|---|---|
| ATCC 11105 | 0 |
| H-9146 | 0.5 |
| H-8683 | 13.4 |
| H-9156 | 15.1 |

What is claimed is:

1. A method for producing L-isoleucine, comprising:

selecting a microorganism belonging to *Escherichia coli* which forms colonies more than 0.6 mm in diameter when cultured in 3 to 7 days at 30° to 35° C. when grown on minimum agar medium containing 0.5 wt. % glucose, 0.02 wt. % L-homoserine, 0.3 wt. % potassium dihydrogen phosphate, 0.6 wt. % disodium hydrogen phosphate, 0.01 wt. % magnesium sulfate, 20 mg/liter calcium chloride, and 2 wt. % agar (pH 7.2) supplemented with 20 mg/liter auxotrophic material and produces L-isoleucine in a nutrient medium;

cultivating said microorganism in said nutrient medium;

producing and accumulating L-isoleucine in said nutrient medium using said microorganism; and recovering said L-isoleucine therefrom.

2. The method according to claim 1, wherein said microorganism is *Escherichia coli* H-9146 or *Escherichia coli* H-9156.

3. A biologically pure culture of *Escherichia coli* H-9146, deposited as FERM BP-5055.

4. A biologically pure culture of *Escherichia coli* H-9156, deposited as FERM BP-5056.

* * * * *